United States Patent [19]

Stupecky

[11] Patent Number: 5,038,621
[45] Date of Patent: Aug. 13, 1991

[54] VARIABLE AREA OBSTRUCTION GAS FLOW METER

[75] Inventor: Josef Stupecky, Irvine, Calif.

[73] Assignee: Bicore Monitoring Systems, Irvine, Calif.

[21] Appl. No.: 569,950

[22] Filed: Aug. 20, 1990

Related U.S. Application Data

[63] Continuation of Ser. No. 432,041, Nov. 6, 1989.

[51] Int. Cl.$^5$ ........................... G01F 1/22; G01F 1/36
[52] U.S. Cl. .................................. 73/861.53; 128/725
[58] Field of Search ........... 73/861.53, 861.54, 861.71, 73/861.74, 861.73; 130/45, 46; 128/725

[56] References Cited

U.S. PATENT DOCUMENTS

| | | |
|---|---|---|
| 2,941,544 | 6/1960 | Peras . |
| 2,989,866 | 6/1961 | Widell et al. . |
| 3,232,288 | 2/1966 | Krobath . |
| 3,989,037 | 11/1976 | Franetki . |
| 4,006,634 | 2/1977 | Billete et al. . |
| 4,083,245 | 4/1978 | Osborn . |
| 4,163,390 | 8/1979 | Rodder . |
| 4,448,064 | 5/1984 | Asayama . |
| 4,599,907 | 7/1986 | Kraus et al. . |
| 4,688,433 | 8/1987 | Silverwater . |

Primary Examiner—Herbert Goldstein
Attorney, Agent, or Firm—Knobbe, Martens, Olson & Bear

[57] ABSTRACT

A flow meter including a variable area obstruction which is mounted in a conduit. Inputs to a differential pressure transducer are positioned in the conduit on opposite sides of the obstruction to measure fluid pressure differential across the obstruction. In one embodiment, a sleeve is secured within the conduit thereof substantially separated from the conduit so as to prevent fluid condensation on the sleeve, and to create a dead end pocket between the conduit and the sleeve for collecting liquids from the conduit end preventing them from contacting the obstruction. The variable area obstruction comprises an elastic membrane that includes first, second and third leaves which extend into the flow stream and are compliant to fluid flow so that an increase in flow rate increases the deflection of the leaves and increases the through flow area through the obstruction. The first leaf is secured at a fixed end adjacent a first portion of the interior surface of the conduit and extends in a first direction to a free end preferably positioned adjacent a second portion of the interior surface of the conduit opposite the first portion. The second and third leaves are located adjacent opposite sides of the first leaf and extend from their fixed ends toward their free ends in directions which are generally opposite to the first direction.

7 Claims, 4 Drawing Sheets

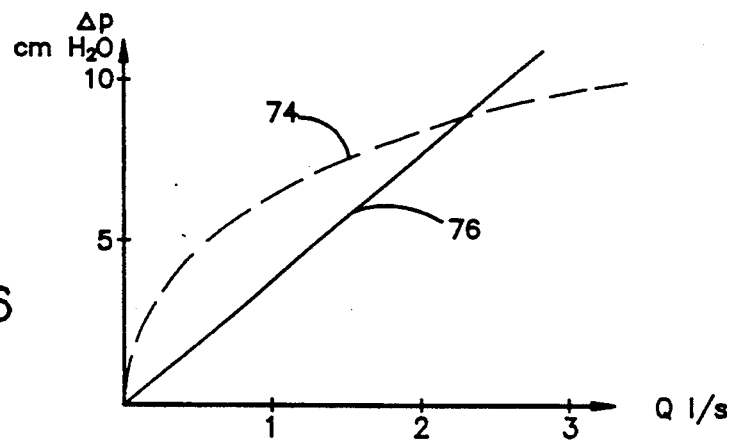
FIG. 6
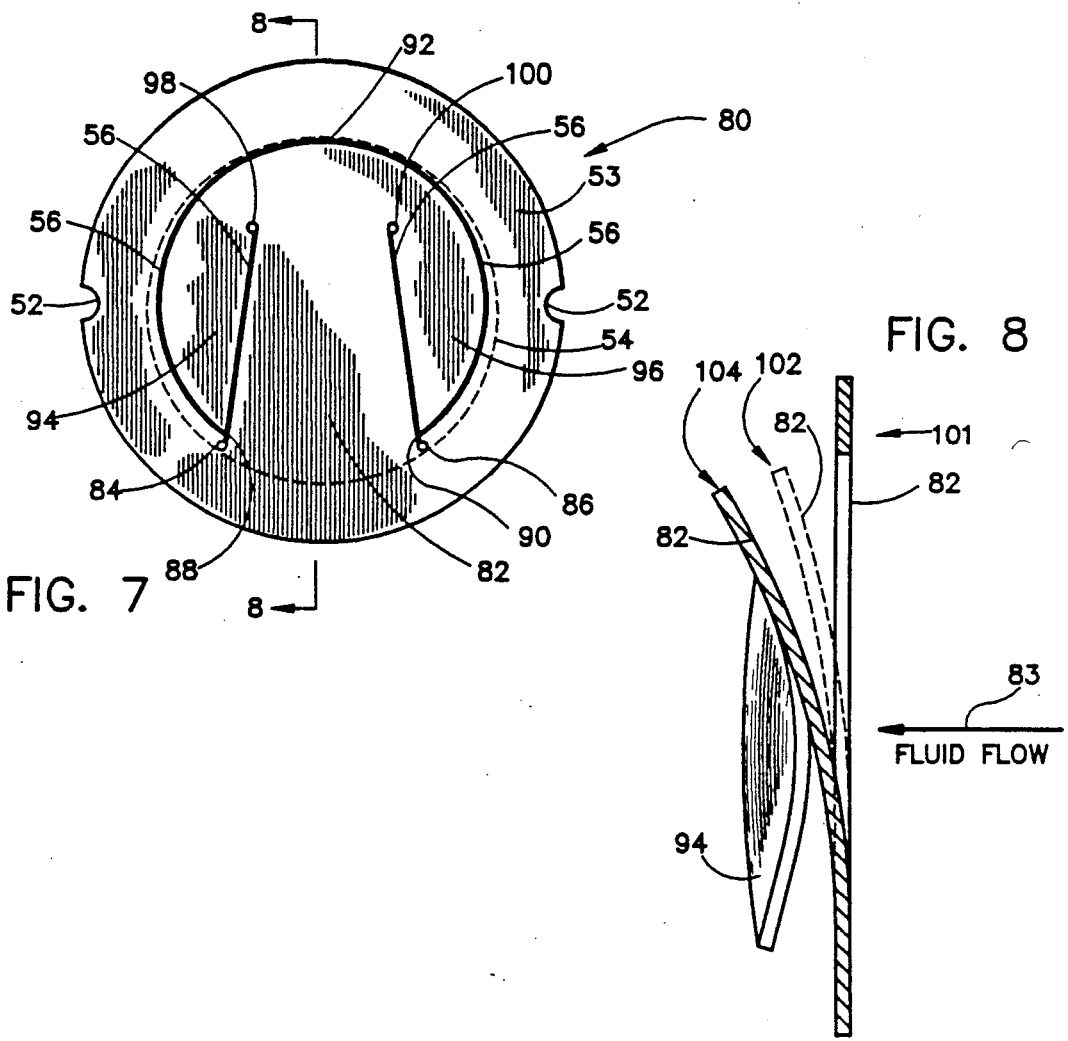
FIG. 7
FIG. 8

VARIABLE AREA OBSTRUCTION GAS FLOW METER

This application is a continuation of application Ser. No. 432,041, filed Nov. 6, 1989.

BACKGROUND OF THE INVENTION

1. Field of the Invention

The present invention relates to flow meters, and in particular to a variable area obstruction in a conduit for use with a pressure transducer, particularly in medical applications, for measuring bi-directional flow rate of fluids such as respiratory gas in the conduit.

2. Prior Art

Long term monitoring of respiratory air flow in critical care patients and in patients during anesthesia is very important for correctly assessing the patient's condition and for selecting the course of his or her future treatment.

The conditions under which this monitoring occurs are not always ideal. For example, in order to monitor this respiratory air flow, a flow meter is typically installed in a breathing conduit in close proximity to a patient. Thus, the flow meter is exposed to a flow of warm air at body temperature that is 100% saturated with water vapor and contains airborne droplets of water, saliva or mucus. These airborne droplets can collect in the flow meter and adversely affect its operation. In addition, since the ambient temperature is always lower than body temperature, water vapor normally condenses on inner surfaces of conduits installed in breathing circuits. The water droplets formed by this condensation glide along the inner walls of the conduit, and frequently collect in, and impede operation of, the flow meter.

Of course, because of the necessity of very accurate and reliable measurements under these circumstances, it is important that the flow meter which is selected meet all of the requirements for proper operation under critical care conditions. In particular, these conditions require use of a very light weight flow meter, with small dead space, with a wide measuring range, and with an accuracy that is not affected by the presence of fluid, including mucus, produced by the patient.

When used in applications where a wide range of breathing flow rates are to be measured, it is very desireable that the flow meter response, as reflected in its output signal, be substantially linear, so that the sensitivity of the meter and accuracy of its readings is the same at low fluid flow rates as at high fluid flow rates. Alternatively, when very low flow rates are being measured, then it is often desireable to produce a flow meter response which changes substantially in response to small changes in the flow rate, thereby enabling more accurate monitoring of the measured flows. In addition, sterility requirements in critical care applications, such as operating room, require that the flow meter be disposable. This dictates a very low production cost, while still necessitating a high sensitivity and accuracy for each individual flow meter.

There are a number of different types of flow meters that are well known among those in the technology and which are acceptable for short term use in applications such as diagnostic pulmonary measurements, due to their linear output signal with respect to the measured flow characteristics. One such device is generally referred to as the Fleisch pneumotachograph, which is the most widely used flow meter for medical applications. This device directs the flow of gas through a bundle of long, small diameter tubes which laminarize the flow. Under laminar flow conditions, the pressure differential is linearly proportional to flow rate. Accordingly, the output signal is generally linear in its characteristics. The sensitivity also remains substantially the same, throughout the range of measurement. However, this device cannot be used for the long term monitoring of respiratory air flow, since moisture or mucus collecting on the bundle of small diameter tubes produces a significant, adverse effect on the output signal of the device. Also, because of the linear response produced throughout the entire range of measurement, this device is not suited for application where a non-linear response is desireable at low flow rates, with a linear response produced at higher flow rates.

Another problem associated with the Fleisch pneumotachograph is its mechanical complexity, which in turn requires a high production cost. The high production cost makes the unit essentially non-disposable. Because it is not disposable, the requirement that the device be cleaned and sterilized after each patient use adds additional cost to the use of this device. The problems encountered in use of the Fleisch pneumotachograph are also experienced in the use of other popular flow meters, such as the ultrasonic, hot wire and turbine pneumotachographs.

Other types of flow meters may be of simple design, but are either too bulky for use in critical care applications, or they produce a non-linear output signal in a flow range where a linear signal is desired, or they have a limited measuring range. These types of flow meters include the fixed orifice, venturi tube and pitot tube meters. More specifically, the fixed orifice flow meter provides an output signal defining a curve which gets progressively steeper as the flow rate increases. This is true since the device operates under turbulent flow conditions, where the pressure differential is proportional to the square of flow rate. This characteristic is undesirable because of drastically reduced sensitivity at low flow rates. Thus, fixed orifice flow meters are generally used in applications having a limited range of flow rates which are likely to be encountered.

Variable obstruction flow meters have also been provided, which combine the simplicity and low cost of the fixed orifice flow meters with better low end sensitivity and linear characteristics that typically have been available only from pneumotachographs. Nevertheless, many existing variable area obstruction designs still suffer from certain drawbacks such as accumulation of moisture or liquids in areas immediately adjacent the variable obstruction. These flow meters have also been known to suffer from resonant vibration or flutter of the leaves which comprise the variable obstruction at low flow rates corresponding to resting breathing of the patient. Furthermore, reduced sensitivity is often experienced at low flow rates due to relatively large leakage area in the obstruction produced by the gaps between the flexible leaves which are apparent when the leaves are in their resting condition. The large leakage area is usually a result of the type of material selected for use as the obstruction, and the manufacturing process selected for producing the obstruction. The material utilized for the obstruction will also determine the obstructions, predisposition to errors caused by unwanted deflection of the leaves due to gravitational or inertial forces.

Based on the above, it would be an important improvement in the art to provide a flow meter having a wide measuring range and accuracy, and which is substantially not affected by the presence of moisture or mucus produced by a patient. It would be a further improvement in the art to provide one embodiment of such a flow meter in which the pressure differential across the obstruction is approximately linearly proportional to the flow rate of fluid in the conduit at very low flow rates as well as at higher flow rates. It would also be an improvement in the art to provide another embodiment of such a flow meter in which the pressure differential across the obstruction varies non-linearly with respect to changes in fluid flow rate in the conduit at very low flow rates, but is approximately linearly proportional to such flow rate changes at higher flow rates. It would be a still further improvement in the art to provide such a flow meter wherein the size of the flow passage in the variable area obstruction is minimized at zero flow condition. It would be a still further important improvement in the art to provide such a flow meter which has a light, simple and inexpensive structure, permitting it to be disposable, while being manufactured in a manner that permits mass production and also maintains the high level of sensitivity and accuracy in each unit produced. A still further improvement in the art would be to provide such a flow meter where the active area of the variable obstruction is substantially the same as the full cross sectional area of the fluid conduit, and the elements of the variable obstruction are shaped in such a manner that they, at maximum deflection, leave a substantially unobstructed passage along the fluid conduit wall.

BRIEF SUMMARY OF THE INVENTION

The present invention comprises a bi-directional flow meter for measuring flow of fluids as a function of pressure differential generated by a variable area obstruction. The flow meter includes a variable area obstruction mounted perpendicular to the fluid flow direction in a cylindrical sleeve installed concentrically within a cylindrical conduit, and a differential pressure transducer having its two sensing ports located on the opposite sides of the obstruction and in communication with the fluid in the conduit.

The cylindrical sleeve extends within the conduit in a configuration that is substantially separated from the walls of the conduit so that it is enveloped by air exhaled from the patient and will approach that air temperature. This avoids fluid condensation on the walls of the sleeve, and creates a dead end adjacent each sensing port. These dead end pockets prevent turbulences localized around and downstream of the variable area obstruction from affecting static pressure readings produced by the differential pressure transducer.

In a preferred embodiment, the variable area obstruction includes three elastic flexible leaves which extend across the diameter of the flow passage in a configuration which is perpendicular to the direction of fluid flow. The leaves are an integral part of a very thin metal diaphragm which forms the variable area obstruction.

The leaves are configured such that the outer most leaves are of asymmetrical shape with their fixed ends defining bases which are anchored to the metal diaphragm in asymmetric orientation adjacent the inner surface of the sleeve. In the absence of fluid flow in the conduit, the outer most leaves extend in a common plane, with their free flexing ends being pointed and curved to substantially conform to the sleeve bore. The center leaf is preferably of trapezoidal configuration, with its fixed end or base being substantially centered about a center line running from its free end to the base. The base is secured adjacent the inner surface of the sleeve along a portion of the inner surface which is opposite to the sensing port. In the absence of fluid flow in the conduit, the center leaf extends toward its free end in a direction opposite to that of the outer leaves, so as to lie between the outer leaves and in parallel configuration with them. The free end of the center leaf is defined by an arch which extends adjacent to the inner surface of a portion of the sleeve which is adjacent to the sensing ports.

The leaves deflect under the influence of fluid such as respiratory gas moving within the conduit, such that an increased flow rate increases the deflection of the leaves and, thus, reduces the resistance of the obstruction to the flow. Because of the angular orientation of the fixed portion of the outer leaves with respect to the center line, those outer leaves twist, as well as bend, about their fixed ends, in response to fluid flowing within the sleeve. In contrast, fluid flow through the sleeve does not cause substantial twisting of the center leaf, but just bending about the fixed end thereof. Accordingly, each of the leaves is deflected in a different plane from the others in a manner which brings each of the leaves closer to the inner sleeve surface as the fluid flow rate increases. Because of this shape and disposition of the leaves, which uses substantially all of the sleeve cross sectional area for the active variable obstruction, the pressure differential across the obstruction changes substantially linearly with any change in the rate of flow.

In another preferred embodiment, the variable area obstruction also includes three elastic flexible leaves. In this embodiment, a primary leaf is formed with its fixed end or base being substantially centered about a center line running from the center of its free end to the base. The base is secured adjacent the inner surface of the sleeve along a portion of the inner surface which is opposite to the sensing ports. This primary leaf defines a portion of a substantially circular configuration, wherein the diameter of the circular portion of this leaf is smaller than the inner diameter of the sleeve. The circular portion of the primary leaf is offset with respect to the center of the conduit, so that the free end of the primary leaf is substantially adjacent to a portion of the inner surface of the sleeve in a location which is substantially opposite to the center of the fixed end of the primary leaf. The free end of the center leaf is positioned adjacent to the inner surface of a portion of the sleeve which is near the sensing ports.

A pair of secondary leaves of asymmetrical shape are defined on the primary leaf by a pair of cut lines extending from each side of the base of the primary leaf to termination points on the distal portion of the primary leaf and in a direction angled inward toward the center of the free end of that leaf. Thus, in response to fluid flowing through the sleeve within the conduit, the primary leaf initially flexes about its base, and then the secondary leaves begin to flex about locations on the primary leaf between the termination of the cut lines and the free end of the primary leaf. The primary leaf is the first to respond to fluid flow, with the secondary leaves subsequently beginning to flex. Accordingly, at low flow rates the pressure differential across the obstruction changes in a nonlinear fashion with respect to any change in the rate of any fluid flow through the conduit. However, as fluid flow rate increases to the point that the secondary leaves begin to flex, such flexing causes further changes in the pressure differential across the obstruction to be substantially linear with respect to any further change in rate of fluid flow through the conduit.

The leaves are formed by etching a very narrow continuous gap through the thickness of the diaphragm, creating a gap between the leaf edges and adjacent structures which is very small, in order to minimize leakage of the fluid through the obstruction. Due to this minimal leakage path through the obstruction, sensitivity and accuracy at very low flow rates are drastically improved. The upper range linearity is also improved since the active flexing area of the obstruction is, in the preferred embodiment, approximately 94% of the total conduit area. Therefore, since the leaves are configured in such a manner that they, while deflected, leave a substantially unobstructed passage along the fluid conduit wall, choking of the fluid flow happens at much higher flow rates than occurs in flow meters of other designs. In addition, use of a chemical milling or chemical etching technique in manufacturing the variable area obstruction from a single piece of thin material such as stainless steel allows the gaps between leaves to be formed with very high accuracies, and at very low costs. Thus, the flow meter described herein is of a type which has a light, simple and very inexpensive structure, which is substantially unaffected by the water vapor and liquid present in respiratory air flow, and which can be mass produced while maintaining high accuracy and reliability in reproduction of each unit.

These and other objects and features of the present invention will become more fully apparent from the following description and appended claims taken in conjunction with the accompanying drawings.

BRIEF DESCRIPTION OF THE DRAWINGS

FIG. 6 is a graphical illustration of flow rate versus pressure differential, showing predicted results based upon theoretical characteristics as defined by mathematical formulas representing the flow meter, and also showing actual test results produced by a prototype of the flow meter illustrated in FIGS. 1-4.

FIG. 7 is a front elevational view of another preferred embodiment of an obstruction diaphragm for use in the variable area obstruction flow meter of the present invention, illustrating the obstruction diaphragm when the leaves are not deflected.

FIG. 8 is a side sectional view of the obstruction diaphragm, taken along lines 8—8 of FIG. 7, but with the leaves in a partially deflected configuration.

DETAILED DESCRIPTION OF THE PREFERRED EMBODIMENT

The invention is best understood by reference to the figures wherein like parts are designated with like numerals throughout.

Figure 1:
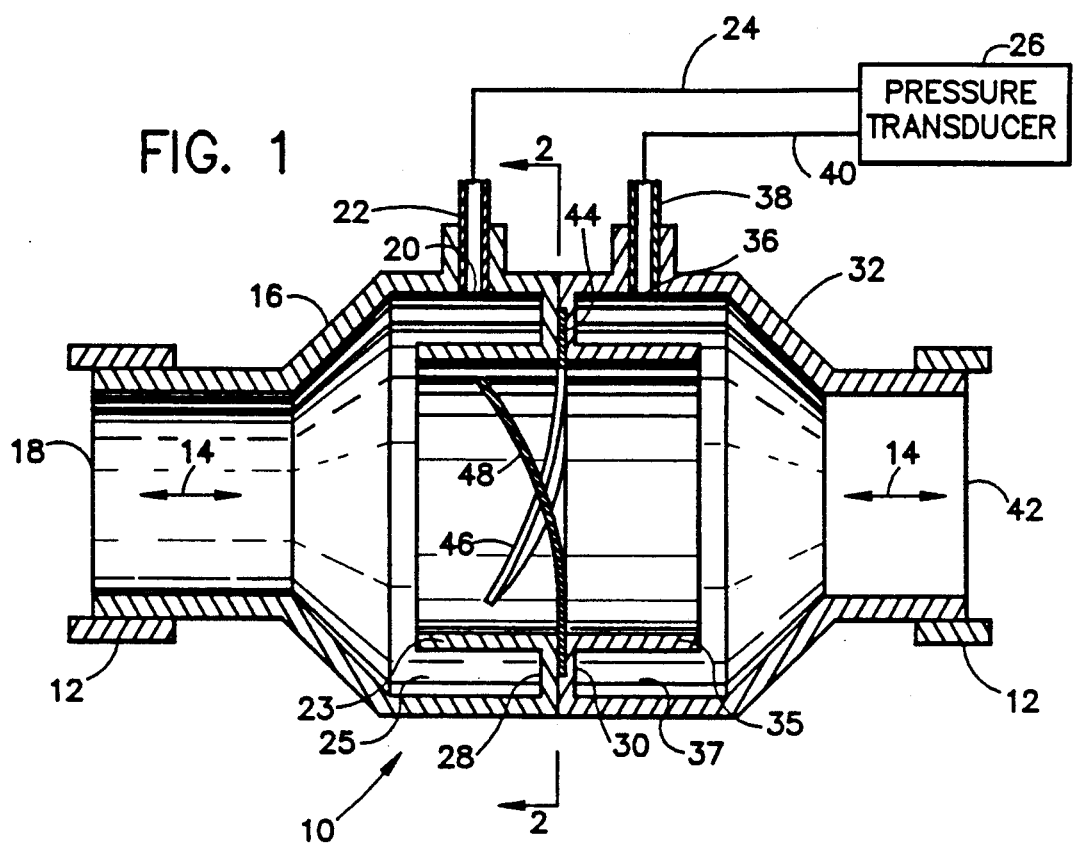
FIG. 1 is longitudinal sectional view of one preferred embodiment of the variable area obstruction flow meter of the present invention.

Referring initially to FIG. 1, a flow meter generally indicated at 10 is interposed in a conduit 12 so as to permit the through flow of fluid through the conduit 12 and the flow meter 10 in the direction of arrows 14. The flow meter 10 comprises a first section 16 which is substantially tubular in configuration, and which defines a first port 18 for communicating fluid between the bore of the first section 16 and the interior of conduit 12.

Extending through the body of the first section 16 is a first pressure port 20. A first tube 22 is connected to the pressure port 20 so as to permit communication of fluid from the first section 16 through the first pressure port 20 and the tube 22 to a first sensor 24 of a differential pressure transducer 26. The differential pressure transducer may comprise any of numerous such transducers which are well know and commercially available in the technology. For example, one preferred embodiment of a differential pressure transducer for use with the present invention comprises a Model NPH-8-015DH manufactured by Nova Sensors, Inc.

Extending inwardly from the first section 16 and, preferably, adjacent to the first pressure port 20, is a first flange or base 28 that supports an inner conduit wall 23 which defines a substantially concentric cylindrical sleeve configuration that extends parallel to the wall of section 16 between the first base and a free edge directed toward the first port 18. The conduit wall 23, base 28 and parallel wall of section 16 form a dead end pocket 25 that extends adjacent to the first pressure port 20.

First base 28 is configured to be received, in mating relationship, with a second flange or base 30 extending inwardly from a second section 32. The bases 28 and 30 are secured together along their adjacent surfaces by chemical or mechanical bonding or by other conventional fastening means.

Preferably, second section 32 is configured as substantially a mirror image of the first section 16, and includes a second pressure port 36 which extends through the surface of the second section 32 so as to provide for communication of fluid from the second section 32, through the second pressure port 36 and through the bore of a second tube 38 connected to the second pressure port 36, to a second sensor 40 which is connected to the differential pressure transducer 26. Fluid is communicated between the interior of the second section 3 and the interior of conduit 12 via a second port 42.

Again, in mirror image configuration with respect to first section 16, the base 30 in the second section 32 supports an inner conduit wall 35 which defines a substantially concentric cylindrical sleeve configuration that extends parallel to the wall of section 32 between the second base 30 and a free edge directed toward the second port 42. The conduit wall 35, base 30 and parallel wall of section 32 form a dead end pocket 37 that extends adjacent to the second pressure port 36.

Figure 2:
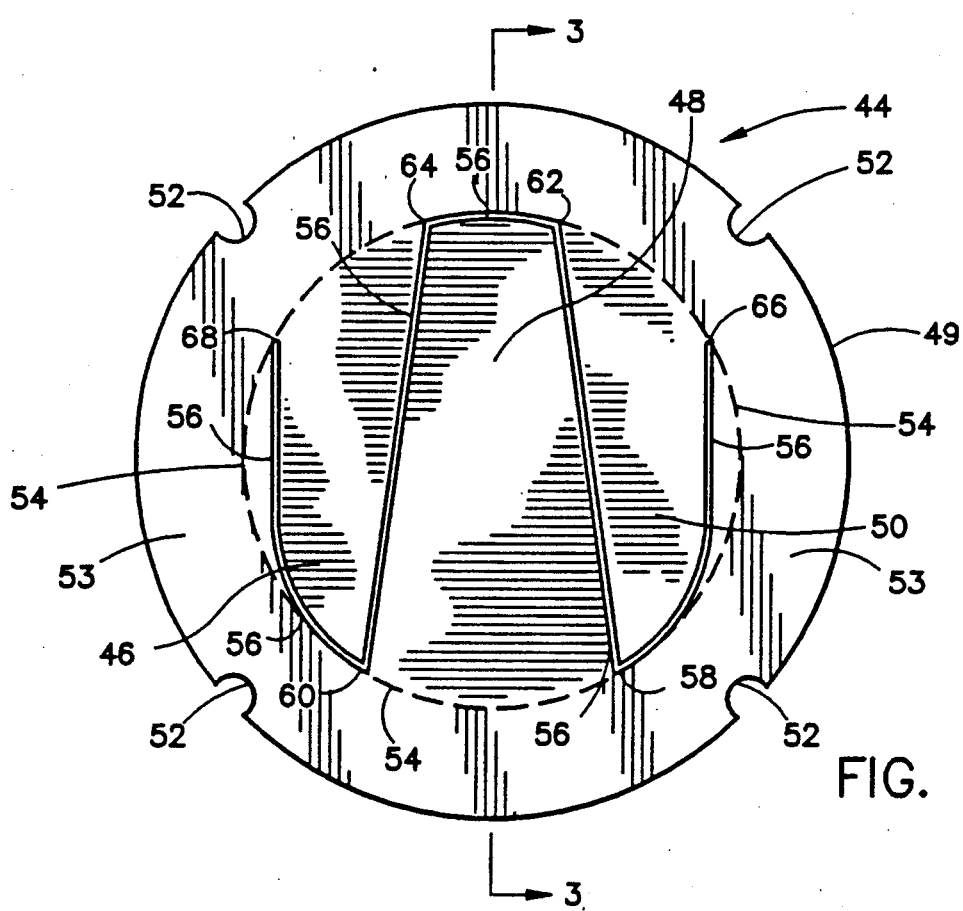
FIG. 2 is a transverse sectional view taken along lines 2—2 of the flow meter of FIG. 1, illustrating the configuration of the leaves in the obstruction diaphragm when the leaves are not deflected.

Portions of the adjacent surfaces of the bases 28 and 30 are preferably constructed so as to receive and secure an outer portion of a variable area obstruction 44, such as that illustrated in FIG. 2. The variable area obstruction 44 comprises a membrane or diaphragm that preferably includes at least three flexible leaves, including a first outer leaf 46, a center leaf 48 and a second outer leaf 50. The leaves 46, 48 and 50 are disposed so as to extend within the bore of sections 16 and 32, interior of the conduit walls 23 and 35 and, in the absence of fluid flow therethrough, to lie in a plane transverse to the direction of fluid flow therein. The leaves 46, 48 and 50 deflect under the influence of moving fluid pressure in such a manner that an increased flow rate increases the deflection of the leaves 46, 48, and 50. For example, in the embodiment of FIG. 1, fluid flow through the flow meter 10 from port 42 to port 18 would cause a deflection of the leaves 46, 48 and 50 in the direction and manner illustrated in FIG. 1.

In operation, the inner conduit walls 23 and 35 define a conduit bore which, because it is substantially separate from the walls of sections 16 and 32, is substantially free from condensation. Specifically, the configuration of the bases 28 and 30 and inner conduit walls 23 and 35 provide an inner conduit surface adjacent the leaves 46, 48 and 50 which is insulated from the ambient temperature communicated through the walls of sections 16 and 32. In this configuration, the inner conduit walls 23 and 35 are enveloped by exhaled air, causing them and the leaves 46, 48 and 50 to assume the temperature of that exhaled air. Thus, condensation does not occur on those surfaces and, therefore, condensed liquids are not transmitted from the walls 23 and 35 to the leaves 46, 48 and 50. Accordingly, interference in the leaf operation due to condensation is substantially avoided.

Of course, the inner conduit or sleeve formed by bases 28 and 30 and inner conduit walls 23 and 35 could also be formed by other structural configurations to produce an insulated inner conduit surface. For example, the bases 28 and 30 which, in the illustrated embodiment, extend about the central periphery of the sleeve, could be located in a different position. Alternatively, other insulating material could be provided to support the sleeve, and could be located in at least a portion of the area between the walls of section 16 and 36 and the inner conduit walls 23 and 35.

In addition to avoiding the problem of condensation on bore surfaces adjacent to the leaves 46, 48 and 50, the separation of the inner conduit walls 23 and 35 from the conduit walls of sections 16 and 32 prevent condensation from other portions of the flow meter 10 from influencing the operation of the leaves 46, 48 and 50. In particular, liquid adhering to the inner walls of sections 16 and 32 and gliding along the conduit surfaces in other areas of the system will not reach the area occupied by leaves 46, 48 and 50, since this liquid will become trapped in one of the end pockets 25 or 37. Those end pockets 25 and 37 also extend adjacent the pressure ports 20 and 36 so as to separate those pressure ports from direct communication with the through flowing fluid within the flow meter 10, and thus preventing turbulences localized around and downstream of the leaves 46, 48 and 50 from affecting the static pressure readings produced in the pressure transducer 26.

The configuration of the variable area obstruction 44 can be more clearly understood by reference to FIG. 2. In particular, the variable area obstruction 44 preferably comprises a diaphragm constructed of an elastic material such as very thin stainless steel shim. In one preferred embodiment, the obstruction 44 is approximately 0.001 inches in thickness. The outer perimeter of the obstruction 44 is substantially circular, and includes at least one indexing cutout 52 for use in properly positioning the obstruction 44 between the sections 16 and 32. Corresponding indexing guides such as matched ridges and indentations or detents on adjacent surfaces of bases 28 and 30 can be provided to register the cutouts in proper positions. A support border 53 is sandwiched between the mating surfaces of flanges 28 and 30 to structurally secure the obstruction 44 in position between sections 16 and 32. With the variable area obstruction 44 secured between sections 16 and 32, the approximate position of the interior surface of the inner conduit walls 23 and 35 with respect to the obstruction 44 is indicated by a dashed conduit bore surface line 54.

The first outer leaf 46, center leaf 48 and second outer leaf 50 are formed in the variable area obstruction 44 by etching a very narrow continuous gap 56 through the thickness of the variable area obstruction 44 along the path indicated in FIG. 2. The width of the gap 56 is exaggerated for clarity. In one preferred embodiment, the gap is approximately 0.001 inches wide, resulting in a leakage area, when the leaves 46, 48 and 50 are in the unflexed state, of approximately 0.0023 square inch. This is at least a twenty fold improvement over the leakage area provided by other commercially available variable area flow meters. The circular outside periphery of the obstruction 44, with indexing cutouts 52 is also formed during the etching operation. The etching operation can comprise any of the well known chemical or electro-chemical etching techniques which are extremely accurate, and do not stretch or deform the material along the edges. Because of this etching technique, the variable area obstruction devices can be mass produced with substantially identical properties.

The leaves 46, 48 and 50 define a configuration which provides a substantially linear change in the pressure difference measured across the variable area obstruction 44 by the transducer 26, with respect to the change in flow rate through the bore of sections 16 and 32. To do this, the leaves 46, 48 and 50 provide a very small amount of leakage area in the absence of fluid flow, while defining a very limited obstruction to fluid flow at high flow rates. This response is achieved as a result of the leaf configuration illustrated in FIG. 2. In particular, the leaves 46, 48 and 50 are arranged so that they extend across the diameter of the conduit bore defined by the inner conduit walls 23 and 35 within sections 16 and 32 in an alternating, intertwining manner.

In one preferred embodiment, the obstruction 44 is secured between sections 16 and 32 so that the leaves 46, 48 and 50 lie within the conduit formed by inner conduit walls 23 and 35 in an orientation wherein the free end of leaf 48 extends toward pressure ports 20 and 22. Generally, the width of the leaves at their free end is smaller than that at their fixed end.

The center leaf 48 is of trapezoidal configuration, with its fixed base defined by points 58 and 60, located adjacent the conduit bore surface line 54, with the base extending generally along line 54 between points 58 and 60. The free end of leaf 48 defines an arch extending generally adjacent the conduit bore surface line 54 between points 62 and 64. In the illustrated embodiment, the distance between points 58 and 60 is twice the distance between points 62 and 64.

The first and second outer leaves, 46 and 50, respectively, are of asymmetrical shape with their free flexing ends terminating in a point at points 58 and 60, and curved along their outward edges to lie adjacent, near their points, to the conduit bore surface line 54. The fixed ends of the first and second outer leaves, 46 and 50, are anchored along those portions of the conduit bore surface line 54 connecting points 62 and 66, and 64 and 68, respectively. Thus, the bases of the outer leaves 46 and 50 are angularly oriented with respect to a center line extending longitudinally along the center of leaf 48.

In the illustrated configuration, the outer leaves 46 and 50 respond to fluid flow through the obstruction 44 by both bending and twisting about their fixed ends, so that as fluid flow increases, the curved outer portions of leaves 46 and 50 tend to remain adjacent to the inner surface of sections 16 and 32. This characteristic of the leaves can be more fully appreciated by reference to FIG. 3. At the same time, the center leaf 48 responds to such fluid flow by bending in a symmetrical manner about its fixed end, with substantially no longitudinal twisting of that center leaf.

With the center leaf 48 extending upwardly within the flow meter 10, as illustrated, airborne droplets of water, saliva and mucus will sink downward to the base of the center leaf 48 and will, therefore, not impede the free movement of the free end of that center leaf 48. This permits the use of the flow meter in a breathing circuit which can be very close to the patient, while minimizing adverse effects of airborne liquids on device operation.

In the configuration described above, the center leaf 48 occupies approximately 44% of the area of the obstruction 44 located within the circular area defined by the conduit bore surface line 54. The outer leaves 46 and 50 each represent approximately 25% of that total area. Thus, the active, or flexible portion of the variable area obstruction 44 which includes the leaves 46, 48 and 50, comprises approximately 94% of the area defined within the conduit bore surface line 54. Accordingly, as the rate of fluid flow increases, the variable area obstruction 44 is able to respond by providing a very limited obstruction to the through passage of fluid, while providing a very minimal fluid leakage path during periods of low fluid flow rate.

Figure 3:
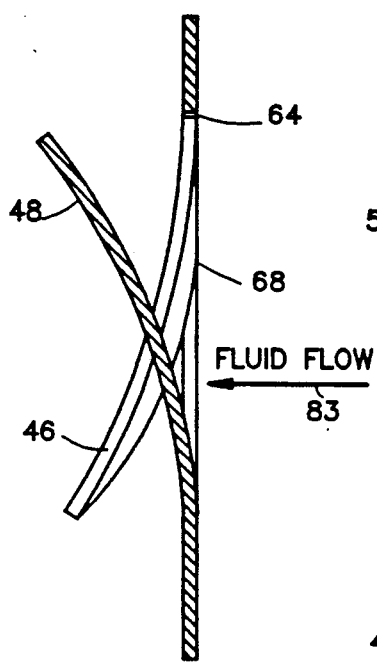
FIG. 3 is a side sectional view of the obstruction diaphragm, taken along lines 3—3 of FIG. 2, but with the leaves in partially deflected configuration as illustrated in FIG. 1.

FIG. 3 illustrates a sectional view of the variable area obstruction 44, with the leaves 46 and 48 partially deflected. From this view, it can be more fully appreciated that deflection of the center leaf 48 produces substantially no twisting, but bending occurs about the fixed end portion of that leaf. In contrast, it is noted that the first outer leaf 46 experiences both bending and twisting about its fixed end, between points 64 and 68. Since the second leaf 50 (not shown) is asymmetrical with respect to leaf 46, it will bend and twist about its fixed end in a different direction. Accordingly, the leaves 46, 48 and 50 lie in different planes, with respect to each other, when they are deflected. This condition results in progressively faster increases in the flow area provided by the variable area obstruction 44 at higher flow rates. This provides for the substantially linear relationship between the change in differential pressure measured by transducer 26 with respect to the change in fluid flow rate through the variable area obstruction 44.

Figure 4:
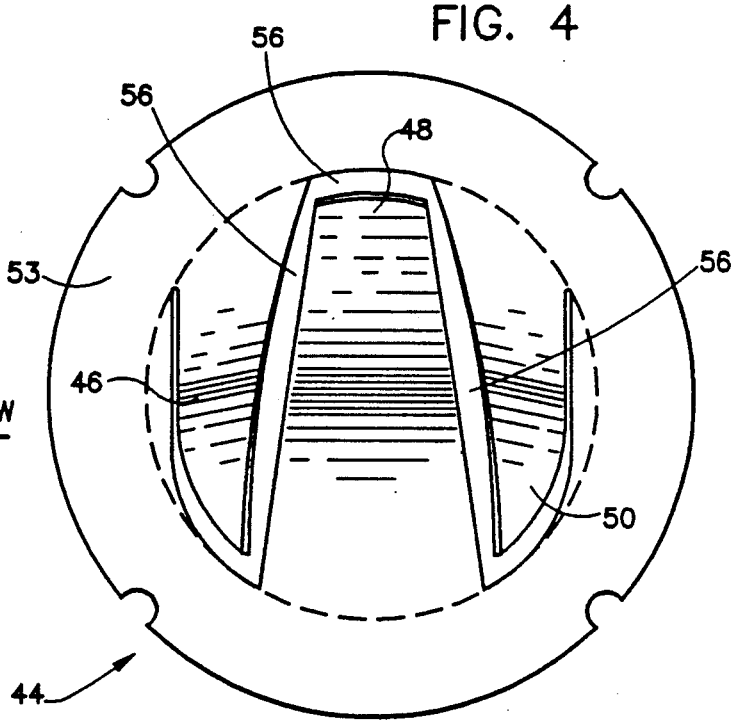
FIG. 4 is a transverse sectional view taken along lines 2—2 of the flow meter of FIG. 1, illustrating the configuration of the leaves in the obstruction diaphragm with the leaves in partially deflected configuration, as in FIG. 3.

By reference to FIG. 4, one may view and more fully appreciate the process whereby the increasing flow area is provided through the variable area obstruction 44 as the leaves 46, 48 and 50 deflect in response to fluid flow as illustrated in FIG. 3. In particular, it is noted that the gap 56 defining the opening between the leaves 46, 48 and 50 widens in response to increased rate of fluid flow through the variable area obstruction 44, to define the through passage for the fluid. It is also noted that the twisting of leaves 46 and 50, along with their bending motion, draws them toward the interior surface of the first section 16 as the fluid flow rate increases. The same situation would be true with respect to the second section 32, if the direction of fluid flow were reversed.

Figure 5:
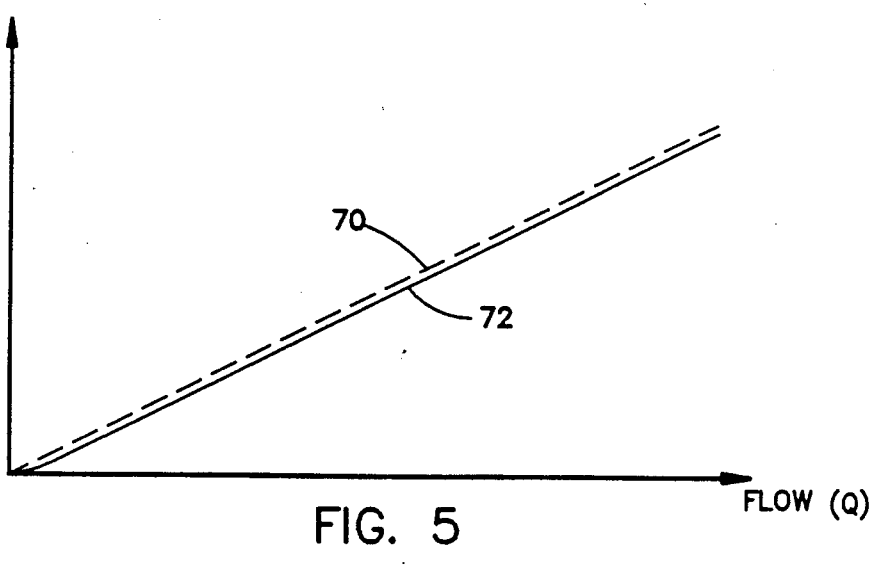
FIG. 5 is a graphical illustration of flow rate versus pressure differential as measured by a flow meter of the type illustrated in FIGS. 1-4.

The performance of the flow meter 10 is graphically illustrated in FIG. 5. In particular, trace 70 represents the ideal characteristic of a flow meter producing a substantially linear relationship between the change in pressure measured through the meter and the change in flow rate. The actual characteristic trace 72 relating to the flow meter 10, is very close to the ideal characteristic trace 70. The trace lines illustrated in FIG. 5 cover a range of flow rates extending from 0.016 liters per second to 2.6 liters per second.

The linearity of the trace line 72 at lower flow rates is a result of the minimal leakage path through the obstruction 44 which is present at those low flow rates. Linearity at the upper end of the flow rates is also improved over other devices, because the active flexing area of the obstruction 44 in the flow meter 10 comprises approximately 94% of the total area within the conduit bore surface line 54. Accordingly, choking of the flow occurs at much higher levels of flow than in devices which do not provide such a large active flexing area of the obstruction.

FIG. 6 illustrates a comparison of the theoretical results represented by theoretical characteristic trace 74 as compared with the actual results determined in testing of a prototype, represented by the actual characteristic trace 76. The prototype flow meter that produced the actual characteristic trace 76 was constructed pursuant to criteria and design parameters listed below:

1. Maximum flow rate required for this specific application was three liters per second.
2. Maximum pressure differential at this flow rate was to be approximately 10 cm $H_2O$.
3. Material for the variable area obstruction 44 was 0.001 inch thick, full hard stainless steel 300 Series.
4. Size of the active area of the variable area obstruction 44 was to be inscribed within a circle of 0.600 inches diameter.
5. The variable area obstruction 44 would be of the three-leaf design, with the leaf unsupported length L=0.582 inch.

The sizing of the variable area obstruction 44 is a complex task. There are many factors which influence the flow versus pressure drop relationship. Secondary turbulences, caused by deflection of the air stream by the flexing leaves and interference of individual streams of air as they merge after passing though the variable area obstruction, create an additional pressure drop which is not accounted for by formulas. The prototype using the variable area obstruction 44 as illustrated in FIGS. 2-4, in accordance with the criteria and design parameters set forth above, produced the following results when tested with ambient air:

| Flow Rate Liter/Sec. | Pressure Differential cm H$_2$O |
|---|---|
| 0.12 | 0.21 |
| 0.19 | 0.50 |
| 0.42 | 1.50 |
| 0.69 | 2.60 |
| 1.02 | 4.00 |
| 1.365 | 5.40 |
| 1.735 | 6.95 |
| 2.160 | 8.70 |
| 2.585 | 10.50 |

The actual characteristic trace 76 of FIG. 6 illustrates a graphical representation of the above results.

In order to build flow meters of different sizes, incorporating the principles of the present invention, a formula which expresses the basic theoretical relationship between flow rate, length of the leaves and pressure differential was developed. In particular, the following formulas established the relationship between flow velocity and pressure differential across an obstruction. Flow rate as a function of variable flow area may then be defined, and this information may then be expressed as a function of fluid pressure and leaf dimensions.

In text "Formulas for Stress and Strain" by R. J. Roark and W. C. Young, Fifth Edition, McGraw-Hill, 1975, pg. 98 case 2a, it is noted that deflection of a flat beam with one end fixed, the other end free, loaded with uniform continuous load is defined by the following:

$$Y = \frac{Wl^4}{8EI} \quad (1)$$

It is also known that:

$$I = \frac{1}{12} bt^3 \quad (2)$$

and:

$$W = p \times b \quad (3)$$

Substituting (2) and (3) into (1) gives the following relationship:

$$Y = \frac{3pl^4}{2Et^3} \quad (4)$$

Where:
y = deflection at free end
l = unsupported length of the beam
E = modulus of elasticity of the beam material
I = sectional moment of inertia at fixed end
t = thickness of the beam
W = unit loading in Lbs per linear inch
p = fluid pressure in cm H$_2$O As the leaf deflects, it forms a triangular flow area along its sides which is proportional to the deflection and the leaf length such that:

$$A = K_A \times y \times l \quad (5)$$

Where:

A = flow area
K$_A$ = area coefficient

From fluid mechanics it is known that:

$$Q = A \times v \quad (6)$$

$$P = K_R \times \frac{v^2}{2g} \quad (7)$$

Where:
v = flow velocity
g = acceleration of gravity
K$_R$ = resistance coefficient
Q = flowrate in liters per second $$\text{From (6) and (7), } Q = A \times \sqrt{\frac{2gp}{K_R}} \quad (8)$$

Substituting (4) into (5) and then (5) into (8) one obtains the following:

$$Q = \frac{3K_A}{2E} \times \sqrt{\frac{2g}{K_R}} \times p1.5 \frac{l^5}{t^3} \quad (9)$$

If all coefficients and constants are condensed into one, the relationship may be expressed as:

$$Q = K \times \frac{l^5}{t^3} \times p^{1.5} \quad (10)$$

The theoretical characteristic trace 74 of FIG. 6 is a graphical representation of the flow rate Q as a function of pressure differential p using Equation 10. From testing the prototype, it was determined that the relationship between the flow rate Q and the pressure differential p is substantially linear. Accordingly, the exponent related to pressure (p) must be equal to 1.0, and not 1.5 as Equation 10 indicates, for the configuration of the variable area obstruction 44 illustrated in FIGS. 2-4. This difference appears to be due to the additional turbulences encountered around the variable area obstruction 44 which were not addressed by the formula. Thus, the modified formula reads:

$$Q = K \times \frac{l^5}{t^3} \times p \quad (11)$$

The numerical value of K for the prototype incorporating the variable area obstruction 44 of FIGS. 2-4 is determined by substituting the test data for that prototype into Equation 11. Thus, from the prototype dimensions and test results defined above, l = 0.582 inch; t = 0.001 inch; Q = 1.735 liters/sec. (a value lower than the maximum was selected to ensure performance within the linear range); p = 6.95 cm H$_2$O. With this information, the value of K is determined to be:

$$K = \frac{Qt^3}{l^5 \times p} = \frac{1.735 \times 0.0001^3}{.5825 \times 6.95} = 3.738 \times 10^{-9} \quad (12)$$

Thus, a formula has been developed which can be used for sizing the flow meter for other flow rates and pressure differentials, as follows:

$$Q = 3.738 \times 10^{-9} \times \frac{l^5}{t^3} \times p \quad (13)$$

For example, for the parameters: Q max=3 liters/sec.; p=9 cm H$_2$O; t=0.001 inch. the diameter of the active area of the variable area obstruction 44 is calculated as follows:

$$L = \sqrt[5]{\frac{Qt^3}{Kp}} = \sqrt[5]{\frac{3 \times .001^3}{3.738 \times 10^{-9} \times 9}} = .6166 \text{ inch} \quad (14)$$

Since the length of the leaf l=0.9253×D, where D is the diameter of the active variable obstruction area:

$$D = \frac{.6166}{.9253} = .666 \text{ inch} \quad (15)$$

Figure 9:
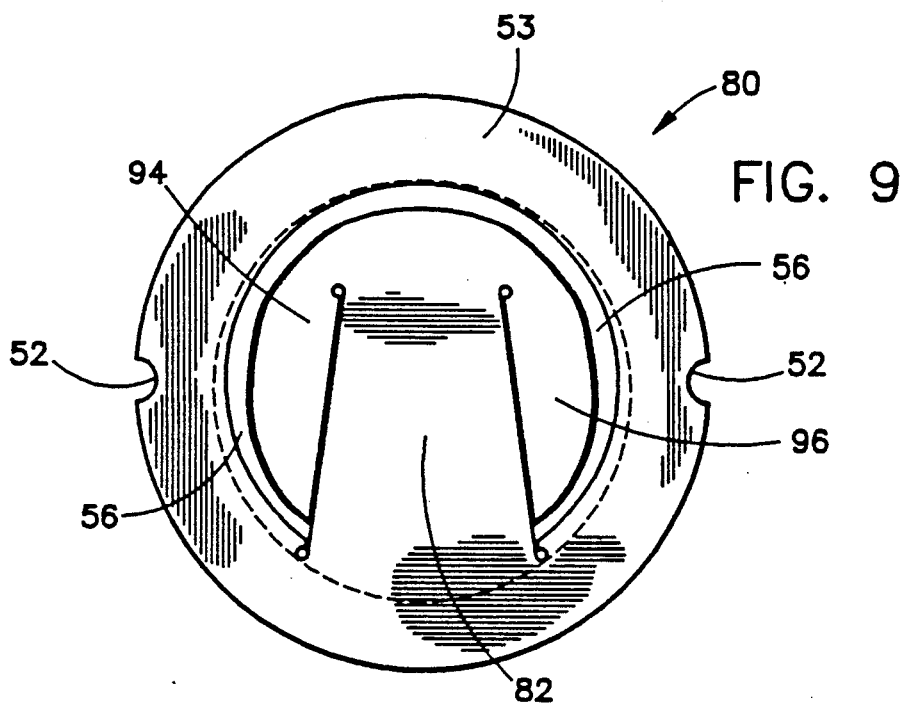
FIG. 9 is a front elevational view of the obstruction diaphragm of FIG. 8, illustrating the configuration of the leaves in the obstruction diaphragm with the leaves in partially deflected configuration, as in FIG. 8.

There are many applications wherein pressure differentials need to be measured at flow rates of one-half liter per second and below across an obstruction. A high degree of accuracy in accomplishing the measurement at these flow rates is very desirable. Accordingly, another preferred embodiment of the invention provides for a substantially linear relationship between the change in pressure differential and change in flow rate at higher flow rates, while having increased sensitivity of the pressure differential with respect to changes in flow rates at low flow rates. This embodiment of the invention is illustrated in FIGS. 7-9.

In particular, FIG. 7 illustrates another preferred embodiment of a variable area obstruction generally indicated at 80, for use in the flow meter of FIG. 1. The variable area obstruction 80 is constructed in a manner substantially the same as that of the variable area obstruction 44, illustrated in FIGS. 2-4, with the exception of the configuration of the leaves in the active flexing area bounded by the conduit bore surface line 54.

Within the active flexing area, the variable area obstruction 80 comprises a primary leaf 82, with its fixed base extending generally along line 54 between points 84 and 86. From points 84 and 86, the parameter of the primary leaf 82 is defined by the very narrow, continuous gap 56 which is etched in the obstruction 80. In particular, from points 84 and 86, the gap 56 travels along a substantially straight, inwardly directed line to points 88, and 90, respectively, defining a short neck between the base and points 88 and 90. Points 88 and 90 are connected to each other by the gap 56 in a manner which forms a substantially circular configuration, within the diameter of the conduit bore surface line 54. The circular portion of the primary leaf 82 is offset with respect to the center of the area within the conduit bore surface line 54, so that the free end 92 of the primary leaf is substantially adjacent to a portion of the conduit bore surface line 54 at a location which is substantially opposite to the center of the fixed end of the primary leaf 82.

A pair of secondary leaves 94 and 96 of asymmetrical shape are defined on the primary leaf 82 by extensions of the gap line 56. In particular, secondary leaf 94 is defined by a portion of the primary leaf 82 which extends outwardly from the center of the primary leaf 82, and lies on the opposite side of a substantially straight extension of the gap 56 running from point 88 to a termination point 98 on the distal portion on the primary leaf 82. Likewise, secondary leaf 96 is defined by that portion of the primary leaf 82 extending outward from the center of the primary leaf, and lying on the other side of a substantially straight portion of the gap 56 extending from the point 90 to a termination point 100 on the distal portion of the primary leaf 82.

The substantially straight gap segments between points 88 and 98 and points 90 and 100, respectively, are directed generally inwardly from the points 88 and 90 to the points 98 and 100, respectively, toward the center of the free end of the primary leaf 82. Thus, the free flexing ends of secondary leaves 94 and 96 terminate at points 88 and 90, respectively. The secondary leaves 94 and 96 comprise a base which is generally defined by the region of the primary leaf 82 which extends generally downwardly and outwardly from the points 98 and 100, respectively, to the gap 56.

The secondary leaves 94 and 96 are arranged so that their fee flexing ends extend in a direction opposite to that of the primary leaf 82, with the base portion of the primary leaf 82 interposed between the free ends of the secondary leaves 94 and 96 so that the leaves are arranged with their free ends oriented in alternately opposing directions.

In the configuration illustrated in FIG. 7, the primary leaf 82 responds to fluid flow through the obstruction 80 by bending about its fixed end in the region defining a neck, between points 84 and 88, and 86 and 90, respectively. The primary leaf 82 does not experience substantial twisting.

The secondary leaves 94 and 96 respond to fluid flow through the obstruction 80 by both bending and twisting about their fixed ends, so that as fluid flow increases, and as the primary leaf 82 bends about its fixed end, the secondary leaves 94 and 96 bend and twist about their fixed ends so their free ends are deflected in a generally inwardly direction, such that the curved outer portions of the secondary leaves 94 and 96 tend to remain adjacent to the inner surface of sections 16 and 32.

In the configuration illustrated in FIG. 7, the initial response to fluid flowing through the conduit at lower flow rates is that the primary leaf 82 initially flexes about its fixed end. No substantial independent flexing is exhibited by the secondary leaves 94 and 96 at the low flow rates. The flow rates creating this response vary depending on the size of conduit and other variables as was discussed in connection with the embodiment of FIGS. 2-4. However, for example purposes, low flow rates through a conduit of about 0.60 inch diameter would be in the range of 0 to 0.5 liters per second.

As the flow rate increases further, the secondary leaves 94 and 96 begin to flex about their fixed locations on the primary leaf. Accordingly, at low flow rates, the pressure differential across the obstruction changes at a rate which is greater than the change in the rate of fluid flow, thus creating a non-linear response at low flow rates. However, as flow rates through the obstruction 80 increase to the point that the secondary leaves 94 and 96 begin to flex, that additional flexing increases the rate at which an opening is created through the obstruction 80, so that the further changes in the pressure differential across the obstruction 80 are substantially linear with respect to further changes in the rate of fluid flow through that obstruction 80.

With the circular portion of the primary leaves 82 offset with respect to the center of the area defined by the conduit bore surface line 54, a bending region is created at the neck adjacent the base of the primary leaf 82. Sufficient space is also thereby provided between the inner surface of sections 16 and 32 and the active flexing area of the obstruction 80, so that the primary leaf 82 and the secondary leaves 94 and 96 can respond to increased fluid flow by providing a very limited obstruction to the through passage of fluid, while still providing a very minimal fluid leakage path during periods of low fluid flow rate. In fact, as with the prior embodiment, the active, or flexible portion of the variable area obstruction 80, including leaves 82, 94 and 96, comprises approximately 94% of the area defined within the conduit bore surface line 54.

By reference to FIG. 8, the response of the primary and secondary leaves with respect to fluid flow can be more fully appreciated. In particular, when there is substantially no fluid flow through the variable obstruction 80, the leaves 82, 94 and 96 lie substantially parallel in plane 101, which is substantially transverse to the direction of fluid flow indicated at 83.

The leaf position at low fluid flow rates is generally illustrated at 102, by phantom lines. In this configuration, it is noted that the primary leaf 82 is bending, without substantial twisting, about the neck region defined at the fixed end of the primary leaf 82, but no substantial bending or flexing of the secondary leaves 94 and 96 is experienced. The leave position at higher rates of fluid flow through the obstruction 80 is illustrated generally at 104. In this condition, the primary leaf 82 is more fully flexed in a bending configuration about the neck adjacent its fixed end. The secondary leaves 94 and 96 (not shown) also both bend and twist about their fixed ends, in the region, respectively, between point 98 and the adjacent gap 56, and point 100 and the adjacent gap 56.

As with the leaves in the embodiment of FIGS. 2-4, the leaves 82, 94 and 96 each lie in different plains with respect to one another, when flexed in response to higher fluid flow rates as illustrated in FIG. 8. This condition results in progressively faster increases in the through flow area provided by the variable area diaphragm obstruction 80 at higher flow rates. However, at low flow rates, the embodiment of FIGS. 7 and 8 provides for a non-linear relationship between the parameters, wherein the change in pressure differential across the obstruction 80 is greater than the change in rate of fluid flow through the variable area obstruction 80.

Referring now to FIG. 9, the increase in size of the passage way through the variable area obstruction 80 defined by the gap 56 is illustrated as it appears at a higher fluid flow rate, corresponding to the condition generally indicated at 104 in FIG. 8.

Figure 10:
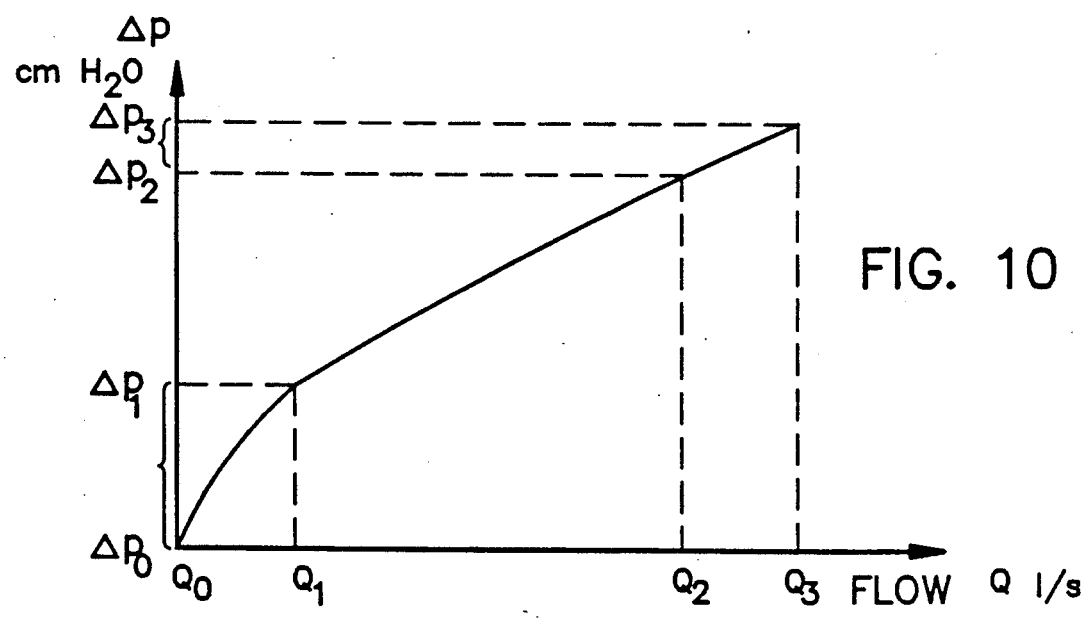
FIG. 10 is a graphical illustration of flow rate versus pressure differential, showing test results produced by the variable area obstruction flow meter of the present invention, using the obstruction diaphragm of FIGS. 7-9.

FIG. 10 provides a graphical illustration of the reverse parabolic configuration which characterizes a plot of flow with respect to pressure differential through the variable area obstruction 80 at flow rates at or less than about one-half liter per second. It is noted that the pressure differential $\Delta p0$ to $\Delta p1$ experienced in the low flow rate region defined between Q0 and Q1 is in the range of about two times as sensitive as the pressure differential $\Delta p2$ to $\Delta p3$ measured in response to the same flow rate changes in the higher flow regions between Q2 and Q3 in the graph of FIG. 10.

In summary, the invention described herein comprises a significant improvement over the prior art by providing a flow meter having a configuration which, in one preferred embodiment, provides a substantially linear relationship between the change in pressure differential across the obstruction and changes in fluid flow rate across that obstruction. Another embodiment is provided wherein a substantially non-linear relationship exists between change in pressure differential and change in fluid flow through the obstruction at lower flow rates, with a substantially linear relationship existing between these elements at higher flow rates. The invention also overcomes other long existent problems in the industry by (1) providing a flow meter having a wide measuring range and accuracy, which is substantially not affected by the presence of moisture or mucus produced by a patient; (2) providing such a flow meter wherein the size of the flow passage in the variable area obstruction is minimized at zero flow condition; (3) providing such a flow meter that has a light, simple and inexpensive structure which permits it to be disposable while being manufactured in a manner that allows mass production while maintaining the high level of sensitivity and accuracy in each unit; and (4) providing such a flow meter where the active area of the variable obstruction is substantially the same as the full cross sectional area of the fluid conduit, and wherein the elements of the variable area obstruction are shaped in such a manner that they, at maximum deflection, leave a substantially unobstructed passage along the fluid conduit wall.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A flow meter comprising:
   a conduit for communicating fluids therethrough and having a first port positioned at a first location in said conduit and a second port positioned at a second location in said conduit, wherein said first and second ports are adapted for connection to a transducer;
   an inner conduit surface located within the conduit and substantially insulated from influence of ambient temperature present outside the conduit, wherein said inner conduit surface prevents exposure of the second port form upstream flow and the first port from downstream flow when flow is in one direction and wherein said inner conduit surface prevents exposure of the first port from upstream flow and the second port from downstream flow when flow is in an opposite direction;
   an obstruction secured within the conduit so that a variable area portion thereof lies within boundaries defined by the inner conduit surface, wherein fluid flow area through said variable area portion increases and decreases in response to corresponding increases and decreases in flow rates of fluid passing therethrough, and
   a sleeve secured within said conduit so that fluids within said conduit flow through said sleeve, with a portion of said sleeve being separated from contact with the conduit and wherein said inner conduit surface comprises an inner surface of said sleeve.

2. A flow meter as defined in claim 1, wherein the sleeve is positioned with respect to the conduit so as to form a dead end pocket between the sleeve and the conduit, so that liquids on interior surfaces of the conduit will collect therein without contacting the obstruction.

3. A flow meter as defined in claim 2, wherein one of the first and second ports is located within a dad end pocket, so as to be substantially protected from fluid turbulences localized around and downstream of the obstruction.

4. A flow meter as defined in claim 2, wherein a first and second end of the sleeve extend away from the obstruction and beyond the first and second port, respectively.

5. A flow meter as defined in claim 1, further comprising:
  transducer connected to the firs and second ports so as to thereby be in fluid communication with fluid flowing through the conduit, for sensing a pressure differential between said first and second ports.

6. A flow meter comprising:
  a conduit for communicating fluids therethrough and having a first port positioned at a first location in said conduit and a second port positioned at a second location in said conduit, wherein said first and second ports are adapted for connection to a transducer;
  an obstruction secured within the conduit having a variable area portion thereof and restricting fluid flow through said conduit such that a first fluid pressure is realized proximal to the first fluid pressure is realized proximal to the first port and a second fluid pressure is realized proximal to the second port;
  an inner conduit surface located within the conduit so as to prevent substantial exposure of the first fluid pressure to the second port and to prevent substantial exposure of the second fluid pressure to the first port, said obstruction housed within boundaries defined by said inner conduit surface, and
  a sleeve secured within said conduit so that fluids within said conduit flow through said sleeve, with a portion of said sleeve being separated from contact with the conduit and wherein said inner conduit surface comprises an inner surface of said sleeve.

7. A flow meter as defined in claim 6, wherein a first and second end of the sleeve extend away from the obstruction and beyond the first and second port, respectively.

* * * * *